US00PP09180P

United States Patent [19]

Hoff

[11] Patent Number: Plant 9,180

[45] Date of Patent: Jun. 27, 1995

[54] VARIETY OF LILIUM NAMED 'INZELL'

[75] Inventor: Petrus M. M. Hoff, Steenbergen, Netherlands

[73] Assignee: Hoffgaarde B.V., Netherlands

[21] Appl. No.: 177,335

[22] Filed: Jan. 4, 1994

[51] Int. Cl.[6] ..... A01H 5/00

[52] U.S. Cl. ..... Plt./87.4

[58] Field of Search ..... Plt. 87.4

*Primary Examiner*—James R. Feyrer

*Attorney, Agent, or Firm*—Webb Ziesenheim Bruening Logsdon Orkin & Hanson

[57] ABSTRACT

A new and distinct cultivar of lily plant named Inzell, particularly characterized by the ivory colored flowers, height of about 90 cm, pedicel 10–12 cm long with 3–5 flowers, glossy leaves, stem bulblets, relative insensitivity to leaf-burning for a white lily, and capable of producing stems and flowers for cut-flower production.

1 Drawing Sheet

BACKGROUND OF THE INVENTION

The present invention comprises a new and distinct cultivar of lily, botanically known as Lilium asiatic and hereinafter referred to by the cultivar name Inzell.

The new cultivar is a product of a planned breeding program which had the objectives of creating new lily cultivars with the capacity to produce stems and flowers for cut-flower production.

The new cultivar was originated from a hybridization made by the inventor Messr. Petrus Mattheus Maria Hoff in a controlled breeding program at Hoffgaarde, B.V., Franseweg 9, 4651 PV Steenbergen, The Netherlands in 1989. The female and male parents were seedlings originated by Applicant, which were proprietary, and maintained by Applicant for breeding purposes.

The new cultivar was discovered and selected as one flowering plant within the progeny of the stated cross by the inventor on May 20, 1991 in a controlled environment in Steenbergen.

The first act of asexual reproduction of the new cultivar was accomplished by the inventor when scales were taken from the initial selection on Oct. 30, 1991 in a controlled environment in Steenbergen.

Horticultural examination of selected units initiated Mar. 20, 1992 has demonstrated that the combination of characteristics as herein disclosed for the new cultivar are firmly fixed and are retained through successive generations of asexual reproduction.

The new cultivar has not been observed under all possible environmental conditions. The phenotype may vary significantly with variations in environment such as temperature, light, intensity, and day length. The following observations, measurements, and comparisons describe plants grown in Steenbergen under greenhouse conditions which approximate those generally used in commerical practice.

The following traits have been repeatedly observed and are determined to be basic characteristics of the new cultivar which in combination distinguish this lily as a new and distinct cultivar.

1) Color of the flowers (ivory).
2) About 90 cm in height.
3) Pedicel 10–12 cm in length with 3–5 flowers.
4) Glossy leaves.
5) Produces stem bulblets.
6) Relatively insensitive to leaf-burning for a white lily.

The accompanying color photographic drawing shows typically flower characteristics of the new cultivar, with colors being as true as possible with illustratives of this type.

In the following description, color references are made to the Royal Horticultural Society Colour Chart. The color values were determined at Steenbergen on Mar. 20, 1992.

THE PLANT

Classification:
- *Botanic.*—Lilium asiatic.
- *Commercial.*—Hybrid asiatic lily for cut flower production.

Form: Single upright stem from each bulb.
Height: About 90 cm.
Growth habit: Upright, erect, strong and vigorous.
Stem:
- *Diameter.*—0.9 cm average.
- *Color.*—Yellow-Green Group 144A.
- *Form.*—Rounded.

Foilage:
- *Quantity.*—90–100 leaves.
- *Size of leaf.*—Up to about 15 cm long and 2.8 cm wide.
- *Shape of leaf.*—Broad elliptic.
- *Texture of leaf.*—Smooth.
- *Color.*—Green Group 139A.

Bulbs:
- *Size.*—12–14 cm in circumference.
- *Color.*—White.

THE BUD

Form: Oblong (UPOV VII).
Size: 8 cm in length.
Color: White Group 155A.

THE FLOWER

Blooming habit: 90 days after planting.
Size: 15 cm in diameter.
Borne: Umbellate, single.
Shape: Oblong (UPOV VII).
Tepalage:
- *Number of tepals.*—6.
- *Arrangement.*—Hexagonal.
- *Color.*—At opening, the mid to outer area is White Group 155A and the inner area is Yellow Group 11B. With time, the tepals tend to be all White Group 155A. The bottom surface is Yellow-White Group 158C.

*Spotting.*—Outer tepals have no spots. Inner tepals have small (0.3 mm) spots, generally 1–5 in number.

*Reflexing.*—None.

*Nectaries.*—Medium in size on the order of 1.5 cm.

Pedicel:

*Length.*—8 cm.

*Color.*—Dark green with some anthocyanin coloring.

*Form.*—Upright.

Texture: Smooth, glossy.

Disease resistance: None.

Fragrance: None.

Lasting quality: Very good.

REPRODUCTIVE ORGANS

Stamens:

*Number.*—6.

*Length.*—7 cm.

*Anthers-color.*—Orange-brown.

*Pollen-color.*—Orange-Red Group 31A.

*Filaments-color.*—White.

Pistils: One, long.

*Color.*—Greyed-Orange Group 171A.

*Stigma-color.*—Light brown.

*Ovaries-color.*—Green.

I claim:

1. A new and distinct variety of lily plant substantially as shown and described.

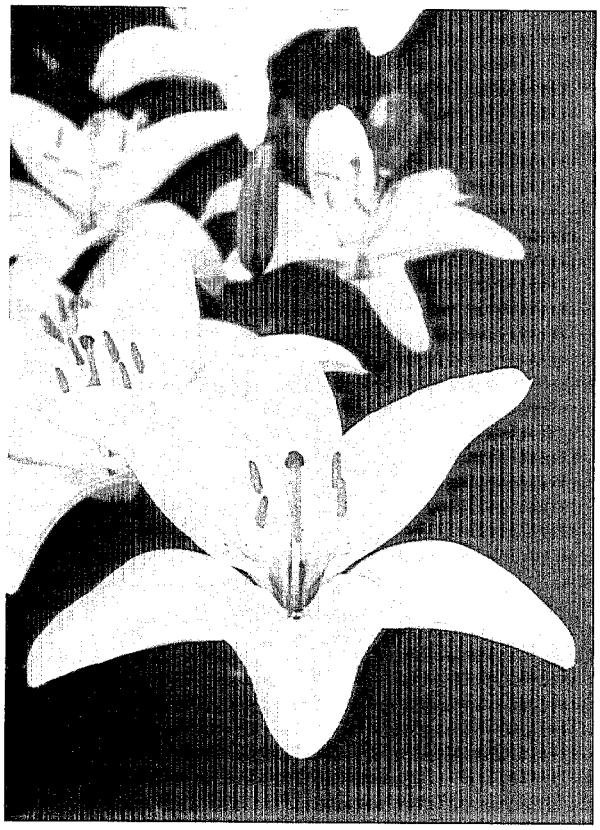

* * * * *